US006770077B2

(12) United States Patent
Van Zile et al.

(10) Patent No.: US 6,770,077 B2
(45) Date of Patent: Aug. 3, 2004

(54) FEMORAL KNEE SAW GUIDE AND METHOD

(75) Inventors: Richard R. Van Zile, Bryan, OH (US); Donald M. Smucker, Perrysburg, OH (US); Thomas M. Coon, Redding, CA (US)

(73) Assignee: NEMCO Medical, Ltd., Hicksville, OH (US)

( * ) Notice: Subject to any disclaimer, the term of this patent is extended or adjusted under 35 U.S.C. 154(b) by 253 days.

(21) Appl. No.: 09/973,584

(22) Filed: Oct. 9, 2001

(65) Prior Publication Data

US 2002/0173797 A1 Nov. 21, 2002

Related U.S. Application Data

(60) Provisional application No. 60/292,425, filed on May 21, 2001.

(51) Int. Cl.[7] .............................................. A61B 17/00
(52) U.S. Cl. ....................................................... 606/88
(58) Field of Search ..................................... 606/86–88

(56) References Cited

U.S. PATENT DOCUMENTS

| | | |
|---|---|---|
| 4,524,766 A | 6/1985 | Petersen |
| 4,566,448 A | 1/1986 | Rohr, Jr. |
| 4,718,413 A | 1/1988 | Johnson |
| 4,722,330 A | 2/1988 | Russell et al. |
| 4,759,350 A | 7/1988 | Dunn et al. |
| 4,841,975 A | 6/1989 | Woolson |
| 4,892,093 A | 1/1990 | Zarnowski et al. |
| 4,935,023 A | 6/1990 | Whiteside et al. |
| 4,938,762 A * | 7/1990 | Wehrli .......................... 606/88 |
| 5,080,675 A | 1/1992 | Lawes et al. |
| 5,122,144 A | 6/1992 | Bert et al. |
| 5,219,362 A | 6/1993 | Tuke et al. |
| 5,234,433 A | 8/1993 | Bert et al. |
| 5,306,285 A | 4/1994 | Miller et al. |
| 5,330,533 A | 7/1994 | Walker |
| 5,342,366 A | 8/1994 | Whiteside et al. |
| 5,364,401 A * | 11/1994 | Ferrante et al. ............... 606/84 |
| 5,417,694 A | 5/1995 | Marik et al. |

(List continued on next page.)

OTHER PUBLICATIONS

European Search Report of Application No. 02011025.0–2318 which corresponds to this U.S. patent application.

*Primary Examiner*—Kevin Shaver
*Assistant Examiner*—Michael B. Priddy
(74) *Attorney, Agent, or Firm*—Emch, Schaffer, Schaub & Porcello Co., L.P.A.

(57) ABSTRACT

A femoral knee saw guide for use in surgery includes a cutting guide having a slot extending therethrough for guiding a saw and alignment structure attached to the guide and positioned externally of the patient's femur for effecting proper alignment of the cutting guide. The cutting guide may be used for cutting one or both condyles at the distal end of the femur in a medial to lateral direction or lateral to medial direction. An arm having a stylus extending into the plane defined by the path of travel of the saw may be used when it is desired to cut only a single condyle to prevent inadvertently cutting the opposing condyle.

45 Claims, 13 Drawing Sheets

U.S. PATENT DOCUMENTS

| | | |
|---|---|---|
| 5,417,695 A | 5/1995 | Axelson, Jr. |
| 5,454,816 A | 10/1995 | Ashby |
| 5,486,178 A | 1/1996 | Hodge |
| 5,520,695 A | 5/1996 | Luckman |
| 5,569,261 A | 10/1996 | Marik et al. |
| 5,601,563 A | 2/1997 | Burke et al. |
| 5,609,639 A | 3/1997 | Walker |
| 5,658,292 A | 8/1997 | Axelson, Jr. |
| 5,662,656 A | 9/1997 | White |
| 5,683,397 A | 11/1997 | Vendrely et al. |
| 5,688,281 A | 11/1997 | Cripe et al. |
| 5,702,466 A | 12/1997 | Pappas et al. |
| 5,720,752 A | 2/1998 | Elliott et al. |
| 5,749,876 A | 5/1998 | Duvillier et al. |
| 5,810,831 A | 9/1998 | D'Antonio |
| 5,830,216 A | 11/1998 | Insall et al. |
| 5,910,143 A | 6/1999 | Cripe et al. |
| 5,911,723 A | 6/1999 | Ashby et al. |
| 5,916,220 A | 6/1999 | Masini |
| 6,013,081 A | 1/2000 | Burkinshaw et al. |
| 6,059,831 A | 5/2000 | Braslow et al. |
| 6,090,114 A * | 7/2000 | Matsuno et al. ............... 606/88 |
| 6,102,954 A | 8/2000 | Albrektsson et al. |

* cited by examiner

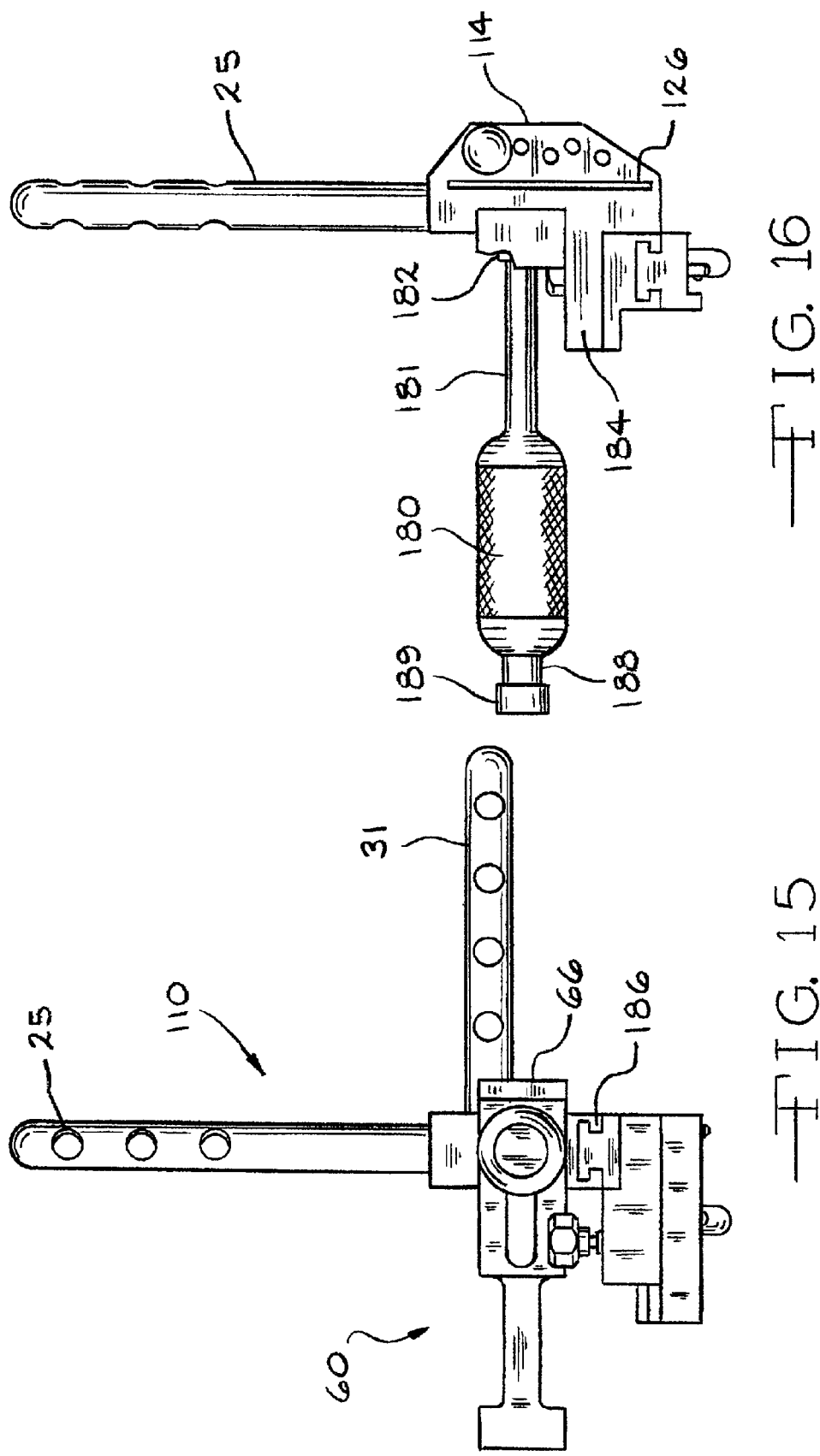

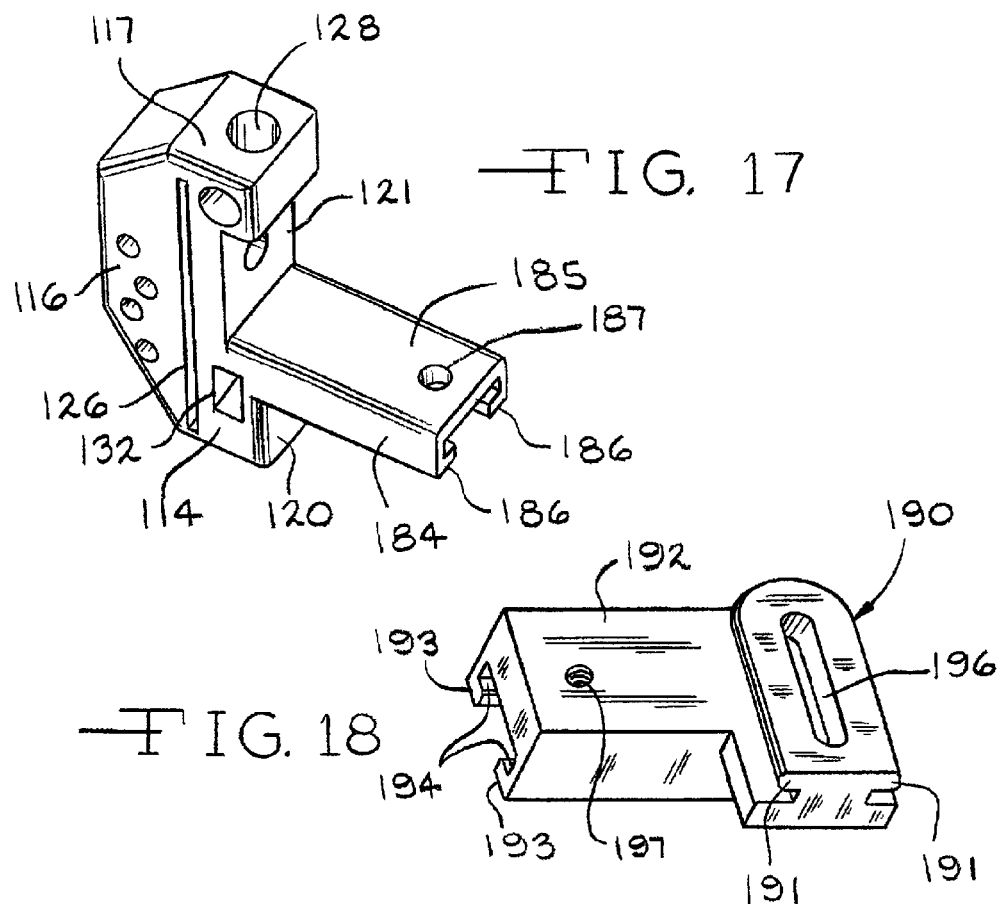
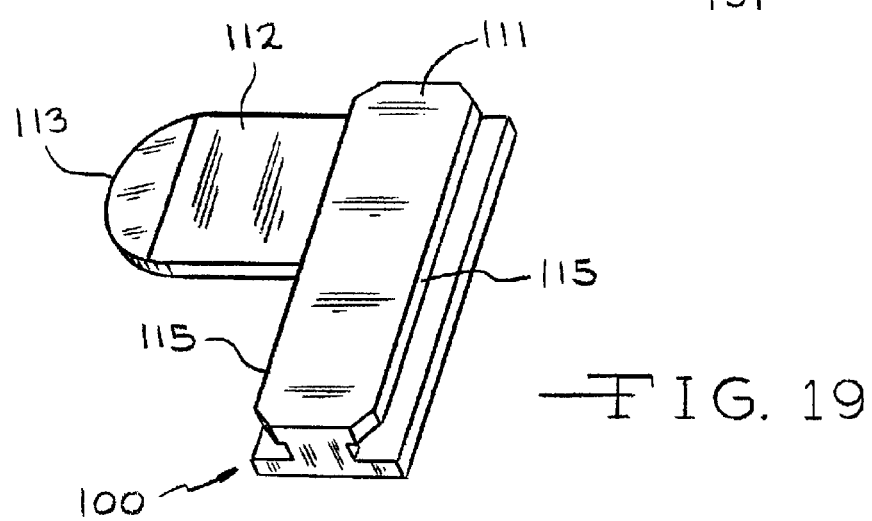

FEMORAL KNEE SAW GUIDE AND METHOD

This Application claims Benefit of provisional 60/292,425 filed May 21, 2001.

The present invention relates to a method and apparatus for performing knee surgery and more specifically to preparation of one or both condyles of a knee to receive a component of a knee prosthesis.

Unicompartmental Knee Arthroplasty (UKA) and Dual-Compartment Arthroplasty (DKA) have evolved into an effective alternative to Total Knee Arthroplasty (TKA) for the treatment of limited osteoarthritis of the knee. In performing UKA, DKA and TKA, it is necessary to precisely cut the condyles of the femur at the tibial femoral joint in order to obtain a satisfactory fit of the femoral component to the distal end of the femur and maintain soft tissue balance and alignment.

BACKGROUND OF THE INVENTION

In UKA, DKA and TKA, it is important that the condyles (condyle in the case of UKA) be cut such that the distal surface facing the tibia is perpendicular to the mechanical axis of the patient's femur. A common procedure in TKA involves drilling a hole in the intramedullary canal several inches along the anatomical axis of the femur starting slightly anterior to the intercondylar notch. The anatomical axis extending from the sulcus at the center of the femur between the condyles to the center of the femoral trochanter is at a slight angle, usually 5 to 6 degrees, to the mechanical axis which extends from the center of the femoral head through the sulcus to the center of the ankle. Following drilling, an alignment rod is positioned in the hole along the intramedullary canal and extends outwardly therefrom. An alignment guide used in combination with the alignment rod directs the cutting instrument along the proper path, anterior to posterior, of the condyles to be cut.

Although drilling a hole in the intramedullary canal is not a major problem, a procedure which avoids such drilling is preferred. Additionally, in conventional procedures for TKA and UKA, the cutting is performed anterior to posterior which may result in cutting or other trauma to the posterior cruciate ligament (PCL) and the anterior cruciate ligament (ACL). A major disadvantage of prior art instrumentation for cutting, in addition to the invasive drilling a hole in the intramedullary canal, is that there is no extra-medullary reference point to assist in making the cut surfaces of the condyles at 90° to the rod extending outwardly from the intra-medullary canal.

SUMMARY OF THE PRESENT INVENTION

The present invention is directed to a surgical procedure with a new approach to UKA and DKA and to extramedullary instrumentation for use in performing such procedure which is designed to be minimally invasive. The instrumentation allows the surgeon to align the femoral component without use of an intramedullary guide hole, thus reducing post operative morbidity and allowing more rapid return to normal function. The present invention includes to an orthopedic saw guide assembly and a method for using which permits precise cutting. The saw guide assembly including the related positioning components are located externally of the intramedullary canal. Accordingly, the apparatus may be characterized as an extra-medullary, minimally invasive unicompartmental/dual-compartmental femoral knee saw guide. It permits precise positioning to obtain a cut which is perpendicular to the mechanical axis while also permitting the cut to be made from medial to lateral or lateral to medial directions. Cutting in a medial to lateral or lateral to medial direction eliminates any need to cut the PCL or ACL, avoids the problem of anterior soft tissue impingement and avoids the need to evert or subluxate the patella. In addition to permitting the patient to return to normal function more rapidly than is possible with anterior to posterior or cutting, the present invention greatly reduces surgical time and effort.

IN THE DRAWINGS

FIG. 15 is a plan view of the cutting guide assembly of FIG. 14.

FIG. 16 is a view similar to FIG. 15 showing the cutting guide assembly rotated 90°.

FIG. 17 is a perspective view of the cutting guide unit of the cutting guide assembly of FIG. 14.

FIG. 18 is a perspective view of combination adjustment member.

FIG. 19 is a perspective view of a foot guide.

DETAILED DESCRIPTION OF THE INVENTION

Figure 1:
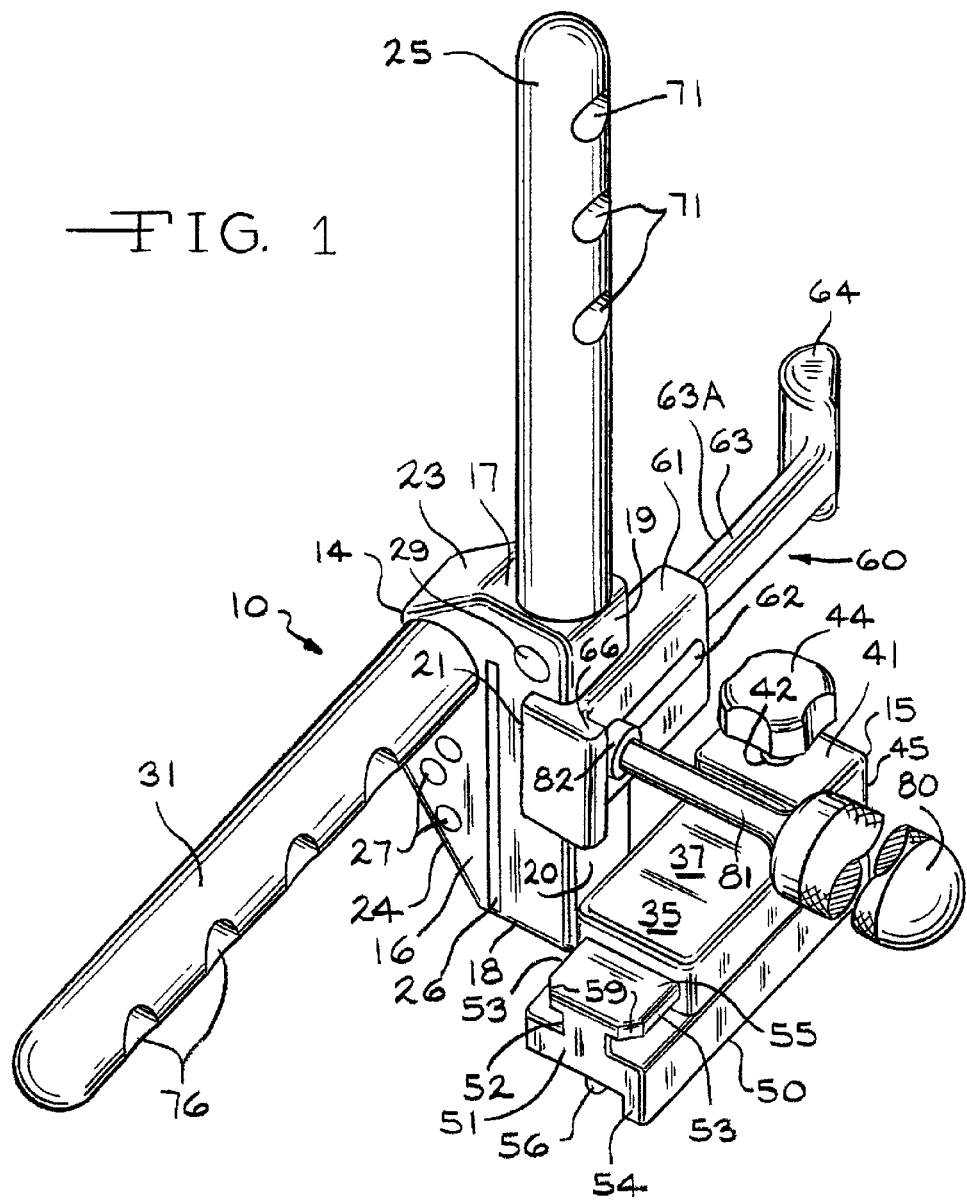
FIG. 1 is a perspective view of one embodiment of cutting guide assembly for cutting the left medial or right lateral condyle.
Figure 2:
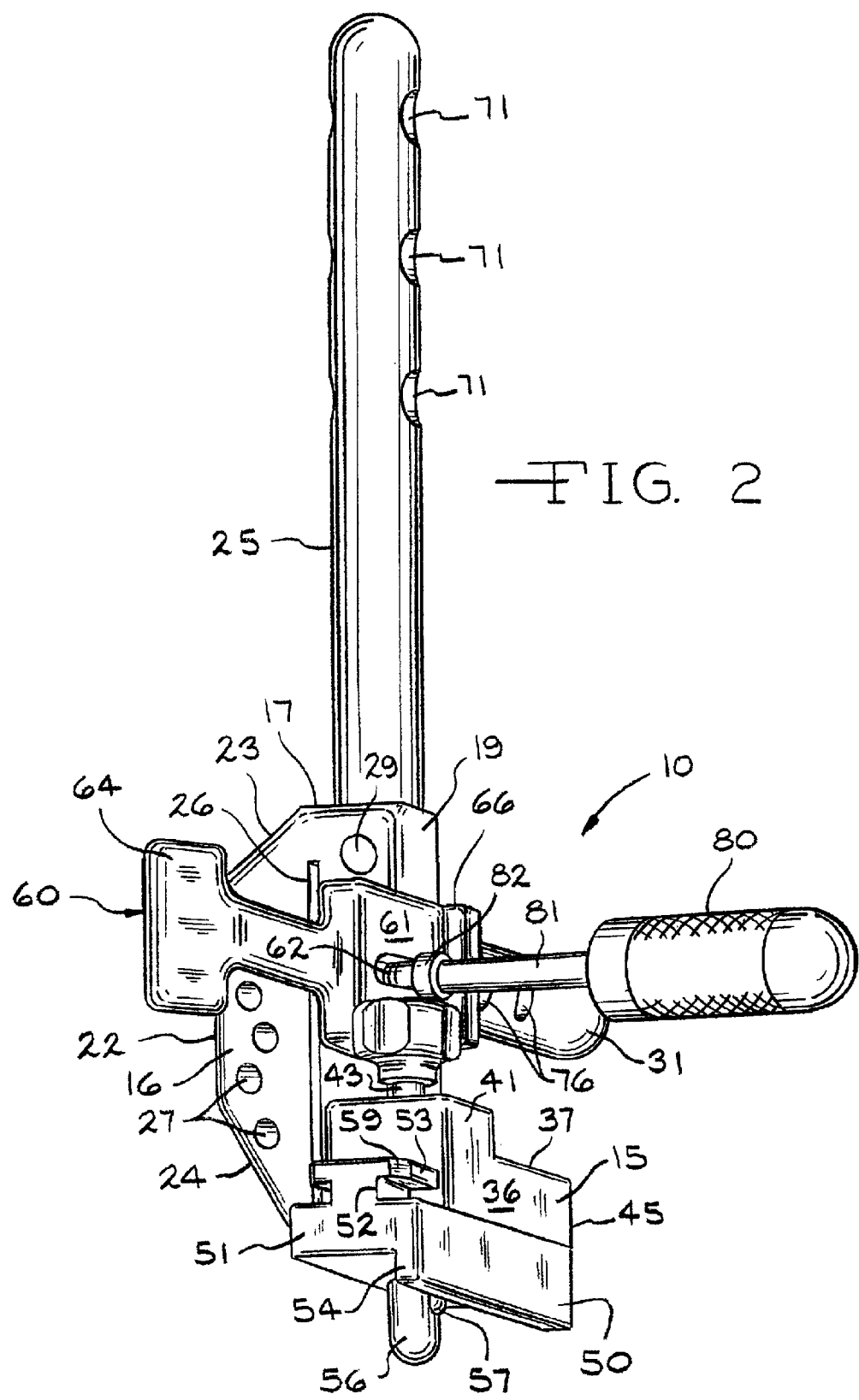
FIG. 2 is a perspective view of one embodiment of the cutting guide assembly for cutting the left lateral or right medial condyle.
Figure 3:
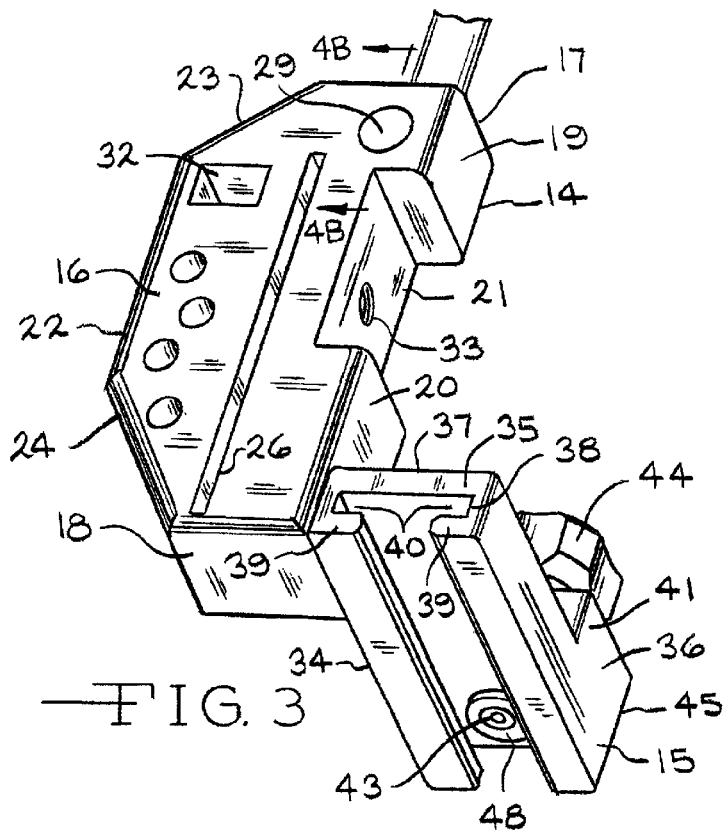
FIG. 3 is a perspective view of the cutting guide subassembly of the cutting guide assembly of FIG. 2.

Referring to FIGS. 1–3, there is shown the extramedullary minimally invasive unicompartmental knee femoral cutting guide assembly 10 of the present invention (hereinafter referred to as "cutting guide assembly"). The cutting guide assembly 10 includes a subassembly having a cutting guide 14 and a plate 15 welded thereto.

The cutting guide 14 has a trapezoidal shape when viewed from the front side 16 or the back side which is parallel thereto. It extends lengthwise from a first end 17 to a second end 18. Adjoining the first end 17 and perpendicular thereto is a planar wall section 19 extending toward the second end 18. Extending from the second end 18 toward the first end 17 is a second planar wall section 20 which is perpendicular to the second end 18 and lies in the same plane as the first planar wall section 19. An elongated recess 21 separates the first planar wall section 19 from the second planar wall section 20. Positioned in the recess 21 is an arm assembly 60, the function of which will be hereinafter described.

Spaced from and parallel to the first and second planar wall sections 19 and 20, is a lateral wall section 22. Extending between the lateral wall section 22 and the first end 17 is a first tapered wall 23 which is disposed at an angle on the order of 50° relative to the plane defined by the lateral wall section 22. Extending from the lateral wall section 22 to the second end 18 is a second tapered wall 24 which is disposed at an angle on the order of 32° relative to the plane defined by the lateral wall section 22.

Extending through the cutting guide 14 is an elongated guide slot 26 spaced substantially midway between and parallel to (i) the first and second wall sections 19, 20 and (ii) to the lateral wall section 22. The slot 26 extends completely through the saw guide 14 from the front 16 to the back and extends approximately 80% of the distance between the first end 17 and second end 18, with one end of the slot 26 being only slightly spaced from the second end 18 and the opposing end being spaced a greater distance from the first end 17. Extending completely through the cutting guide 14 from the front 16 to the back are a plurality of four holes 27 which extend along axes which are substantially perpendicular to the front 16 and alternating pairs of which are parallel to the lateral wall section 22 and positioned in the space between the lateral wall section 22 and the slot 26, with two of such holes 27 lying on a line slightly closer to such lateral wall section 22 than the other two holes 27. The holes 27 receive pins with which the surgeon may fasten the cutting guide 14 to the lateral or medial aspect of the knee undergoing the surgical procedure.

In an area of the guide 14 adjacent to the corner formed by the first end 17 and the first planar wall section 19 and extending inwardly from said first end 17 is a short circular recess 28 (See FIG. 4B) sized to receive an alignment rod support tower 25. The recess 28 for receiving the support tower 25 follows an axis which is parallel to the first planar wall section 19 and ends before reaching the elongated recess 21. Extending inwardly from the front 16, also in a position adjacent the first end 17 and first planar wall section 19, is a hole 29 extending to the short circular recess 28 and sized to receive a pin 46 or screw to fix the support tower 25 in proper alignment for receiving an alignment rod. Preferably, the pin 46 (see FIG. 4B) is permanently mounted in the hole 29 and extends sufficiently far into the recess 28 to engage the flat 74 of the stub 73 of the support tower 25 as will be hereinafter discussed.

Figures 4, 4A, 4B:
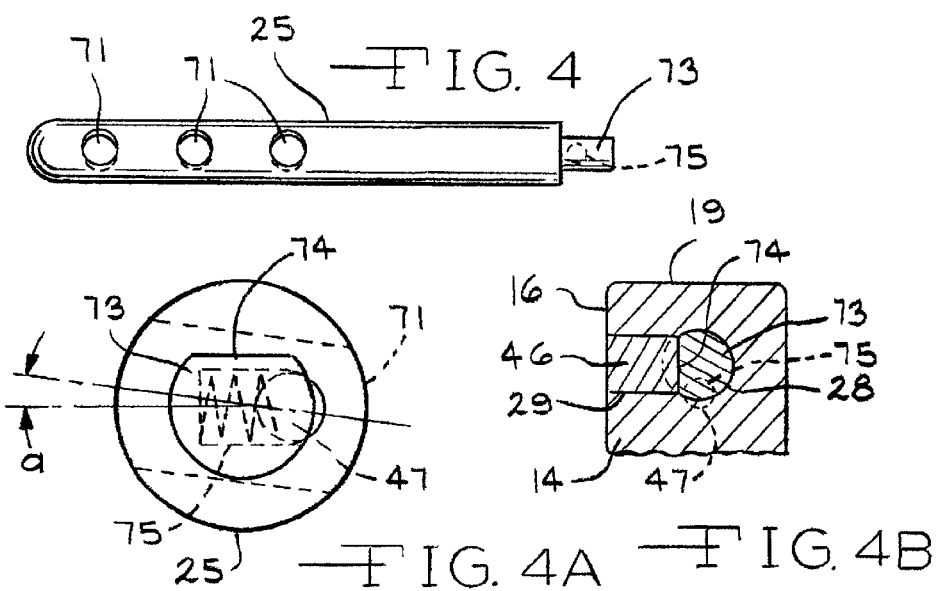
FIG. 4 is an elevational view of an alignment rod support tower.
FIG. 4A is an enlarged end view of FIG. 4.
FIG. 4B is a fragmentary sectional view of the saw guide and the stub of an alignment rod support tower positioned in a recess thereof taken through line 4B—4B of FIG. 3.
Figure 9:
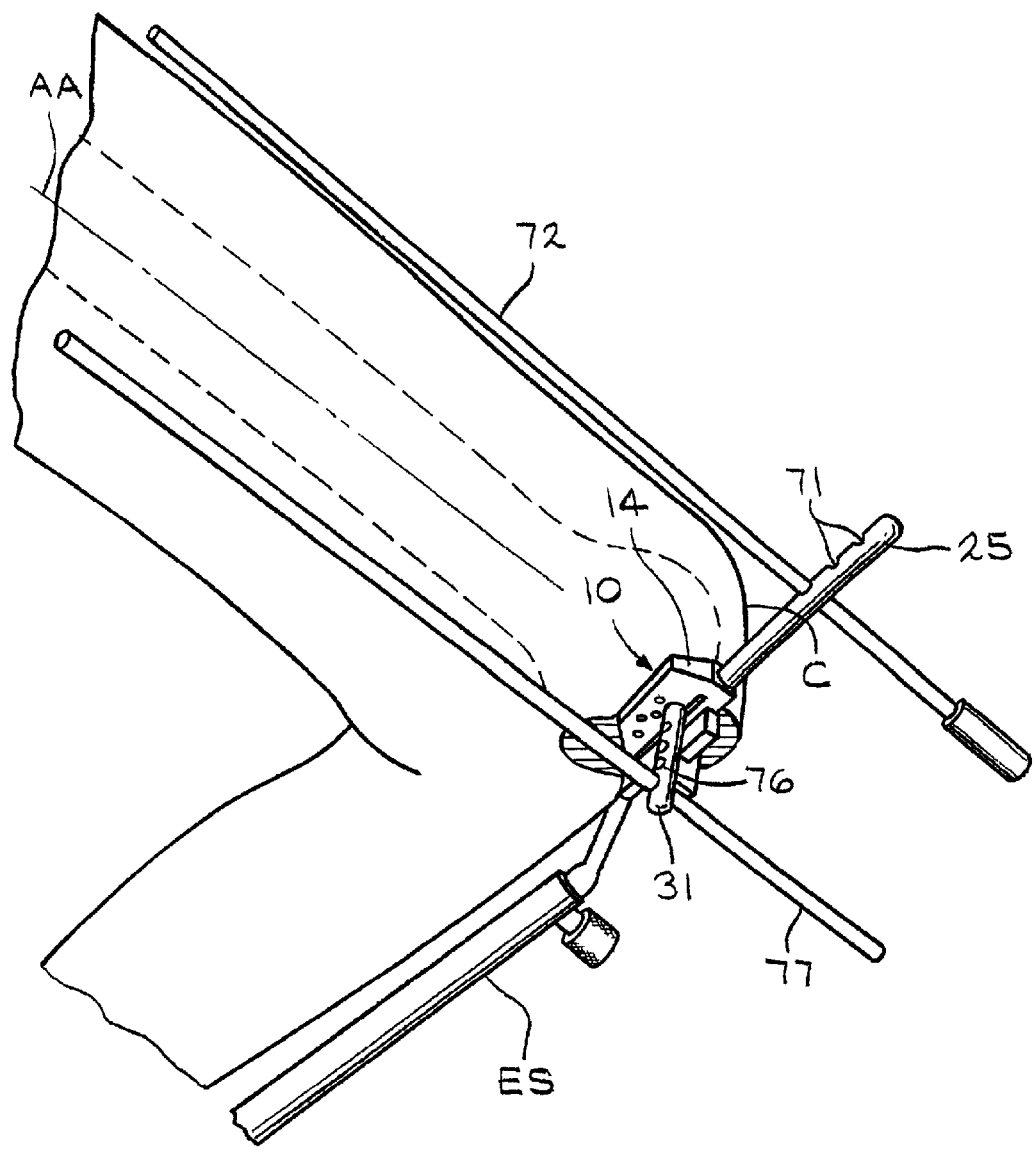
FIGS. 9–13 show various steps in performing UKA and DKA with the instrumentation of the present invention and related support instrumentation.

Referring to FIGS. 4, 4A and 9, the support tower 25 and its alignment relative to the patient and the cutting guide 14 will be discussed. As mentioned in the background of the invention, the anatomical axis of a patient's femur is at a slight angle relative to the mechanical axis. Although such angle is usually in the range of 5 to 6° it can vary between 2° and 8° and, in extreme cases, possibly more. The saw guide 14 and the support tower 25 are designed to assist the surgeon in obtaining a cut which is perpendicular to the mechanical axis. The surgeon can determine for any given patient the approximate angle between such patient's anatomical axis and mechanical axis. The support tower 25 is provided with three holes 71. These holes are intended to receive an alignment rod 72 (see FIG. 9) which the surgeon will move to a position parallel to the anatomical axis AA of the patient. As may be seen in FIGS. 4, 4A and 4B, the support tower 25 has a reduced size end stub 73 designed to be received in the circular recess 28 of the cutting guide 14. The end stub 73 has a cross-sectional configuration which is partially circular but with a flat 74 thereon. The end stub 73 also has a recess 75 for receiving a spring loaded detent 47 for frictionally retaining the stub 73 in the circular recess 28.

As shown in FIGS. 4 and 4A, the holes 71 each lie on an axis which is disposed at the desired angle α relative to the flat 74 for the patient in question. The angle of the support tower 25 used for surgery of a specific patient will be governed by and substantially the same as the angle between that patient's mechanical axis and anatomical axis. As previously discussed, for many patients, that angle is approximately 6°. Accordingly, by positioning the alignment rod 72 extending through the holes 71 of a support tower with the proper angle α for that patient in a position which is parallel to the patient's anatomical axis AA, the cutting guide 14 will be in a position to direct the cutting saw perpendicular to the patient's mechanical axis.

In positioning the end stub 73 in the circular recess 28, it will be necessary to have it rotationally oriented such that end of the pin 46 mounted in the hole 29 engages the flat 74. The engagement of the end of the pin 46 against the flat 74 secures the support tower 25 and its holes 71 in the desired angular position. If it is determined that a patient requires a support tower with holes at a different angle α, say 2° or 4°, it is simple to replace one tower with another having the holes 71 disposed at the desired angle α relative to the flat 74 for that patient.

As will be appreciated by those skilled in the art, the alignment rod 72 extending through one of the holes 71 of the tower 25 provides varus/valgus alignment of the cutting guide assembly 10 by positioning the alignment rod 72 substantially parallel with the upper portion of the patient's femur defining the anatomical axis AA.

Figure 13:
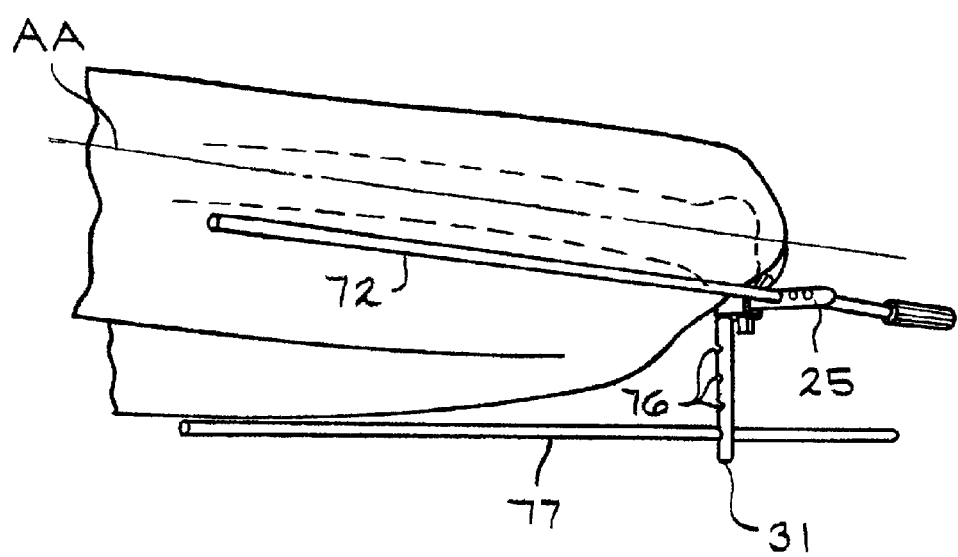
Figure 14:
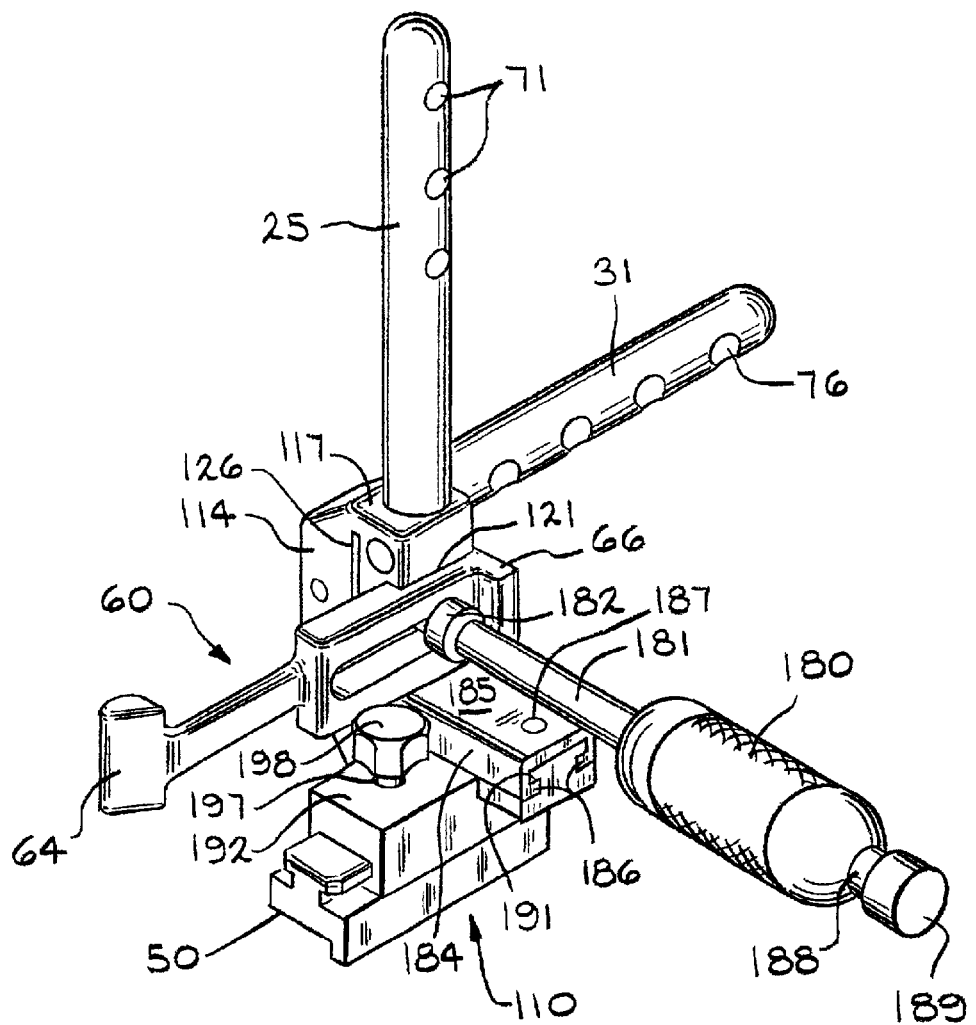
FIG. 14 is a perspective view of a second embodiment of cutting guide assembly.

It is also necessary to align the cutting guide assembly 10 in the coronal plane as viewed in flexion extension. This is accomplished by providing a second support tower 31 extending from the front 16 of the saw guide 14. The saw guide 14 is provided with a recess 32 (see FIG. 3) having a rectangular cross-sectional configuration positioned near the juncture between the lateral wall section 22 and the first tapered wall 23. The second support tower 31 is provided with a rectangular stub which is frictionally engaged in the rectangular recess 32. A plurality of four holes 76 extend through the second support tower 31 at substantially right angles to the axis of the support tower 31. The axis followed by each of the holes 76 is so related to the rectangular stub and the alignment of the rectangular recess 32 in which the stub fits, that an alignment rod such as the alignment rod 77 in FIGS. 9 and 13 extending through any of such holes 76 and positioned parallel to the side of the patient's femur will cause the cutting guide 14 to be positioned correctly with respect to the patient's flexion extension so that a cut made by a saw member 58 (see FIG. 10) extending through the guide slot 26 will make the cut along a plane at right angles to the patient's mechanical axis assuming, of course, that the alignment rod 72 is also properly positioned.

The cutting guide 14 is provided with one additional hole 33 which is threaded and extends from the bottom of the recess 21 toward the guide slot 26 (see FIG. 3).

The plate 15 of the saw guide subassembly is welded to the saw guide 14. The plate 15 has one side, the welded side 34, and an opposed parallel side 36 which extend substantially perpendicular to the front 16 of the saw guide 14. The plate 15 extends from a first end 35 which is parallel to the front 16 and aligned with a chamfer between the front 16 and the second planar wall section 20 to a second end 45. The welded side 34 in the area adjacent end 35 is welded to the planar surface 20 in an area adjacent the second end 18. In cross-section as viewed from the end 35, the plate 15 has an upper panel 37, a pair of spaced apart legs 38 extending downwardly from such upper panel 37 each of which has an in-turned flange 39 extending therefrom. The in-turned flanges 39 cooperate with the upper panel 37 to define a pair of slots 40.

The plate 15 has a raised platform 41 extending from the upper panel 37 adjacent the second end 45. The raised platform 41 is provided with a threaded aperture 42 to which is threadedly engaged the stem 43 of a rotatable knob 44. A washer 48 is mounted on the end of the stem 43.

Slideably engageable in the slots 40 of the plate 15 is a base member 50. The base member 50 has a main body portion 51, a reduced size connector portion 52 and a pair of wings 53 extending outwardly from such reduced size connector portion 52. The wings 53 are receivable in the slots 40 of the plate 15 and are provided with chamfers 59 at each corner to assist in positioning in the slots 40 of the plate 15. The base member 50 may be retained in a fixed position on the plate 15 by rotating the knob 44 to snugly engage the end of the stem 43 and its washer 48 against the top 55 of the base member 50 following sliding it in the slots 40 to the desired medial to lateral position. Extending from one side of the main body portion in a direction opposite that of the wings 53 is a leg 54. Affixed to the main body portion 51 and extending downwardly therefrom (as viewed in FIGS. 1 and 2) is a locator 56 and a pin 57 which are designed to engage a commercially available external support to be hereinafter discussed.

Figure 7:
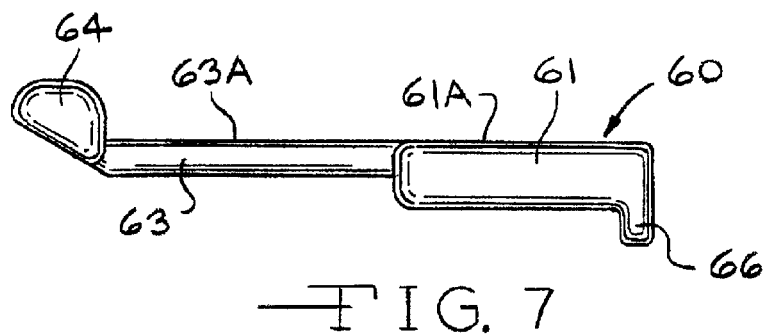
FIG. 7 is a view of one arm of the assembly for determining a certain depth of cut for a condyle.

Referring FIGS. 1, 2, 7 and 8, there is shown the arm assembly 60 and its relationship to the other components. The arm assembly 60 includes a generally rectangular connector portion 61 sized to be slideably received in the recess 21 of the saw guide 14. The connector portion 61 includes an elongated slot 62 which is positioned to overlie the threaded hole 33 at the bottom of the recess 21. As shown in FIGS. 1, 2 and 7, extending from the connector portion 61 is a reduced size arm 63 extending along the same axis as the elongated slot 62. The arm 63 has a surface 63A which is coplanar with the surface 61A of the connector portion 61. An integral stylus 64 is at the end of the arm 63 remote from the connector portion 61. The stylus 64 extends upwardly from (as viewed in FIG. 7) the plane defined by the common surface 61A of the connector portion 61 and 63A of arm 63. When positioned in the recess 21 of the saw guide 14, the surface 61A engages the bottom of the recess. The arm assembly 60 is slideably retained in the recess 21 of saw guide 14 by a handle 80 having a threaded stem 81 threadedly engaged in the threaded hole 33. The stem 81, which extends through the slot 62 of the arm assembly, is provided with an enlarged shoulder 82 which engages the upper surface of the arm assembly connector portion 61.

The positioning of the stylus 64 which extends outwardly from the plane defined by the surface 61A is such that it will be aligned with the plane of the cutting guide slot 26 and thereby prevent a saw 58 extending through the cutting guide slot 26 from moving beyond the stylus 64 following the cutting one condyle. The stylus 64 is designed to fit into the sulcus between the condyles of a patient and thus permits the cutting of one condyle but prevents the inadvertent continuation of the saw 58 into the opposing condyle. This may be seen in FIG. 10. Preferably, the arm assembly 60 is provided with a lip 66 which extends downwardly (as viewed in FIG. 7). The lip 66 provides an abutment by which the surgeon can readily slide the arm assembly 60 to the desired position.

The extradumedulary cutting guide assembly 10 is designed such that it can be attached to a conventional external support attached to the tibia. Such external supports are well known in the art. The base member 50 which is slideably received in the plate 15 provides means for such engagement with the locator 56 and pin 57.

In use, the surgeon attaches the base member 50 to the tibial attachment conventional external support ES (see FIG. 9) following exposure of the patient's condyles C. With the saw guide assembly so attached, the saw guide 14 and plate 15 may be moved medially to laterally or laterally to medially by sliding on the base member 50 to the appropriate position with the side of the saw guide 14 from which the arm assembly 60 extends in contact with the medial or lateral side of the knee undergoing surgery. When so positioned, the surgeon will turn the knob 44 to tighten the plate 15 into a fixed positioned relative to the base member 50.

An alignment rod 72 extending through one of the holes 71 of the first support tower 25 is moved to a position parallel to the patient's anatomical axis AA while at the same time moving the second alignment rod 77 positioned in one of the holes 76 of the second support tower 31 to a position parallel to the patient's femur as viewed from the side. Such movement of the alignment rods 72 and 77 and their respective support towers 25 and 31 serves to move the saw guide 14 into proper alignment to obtain a cut which is perpendicular to the mechanical axis.

In order to obtain the appropriate depths of cut, the arm assembly 60 is so constructed relative to the saw guide 14 and its guide slot 26 as to position the saw guide 14 for the proper cutting depths. For many patients, it is desirable to cut approximately 6 millimeters off of the distal end of the condyle; however, depending upon the condition of the patient's knee, it may be desirable to cut less or more, possibly as much as 10 millimeters. For most patients, the positioning to obtain the appropriate depth of cut will result from contact between the edge 63A of the reduced size arm 63 against the distal end of the condyle C to be cut.

Figure 10:
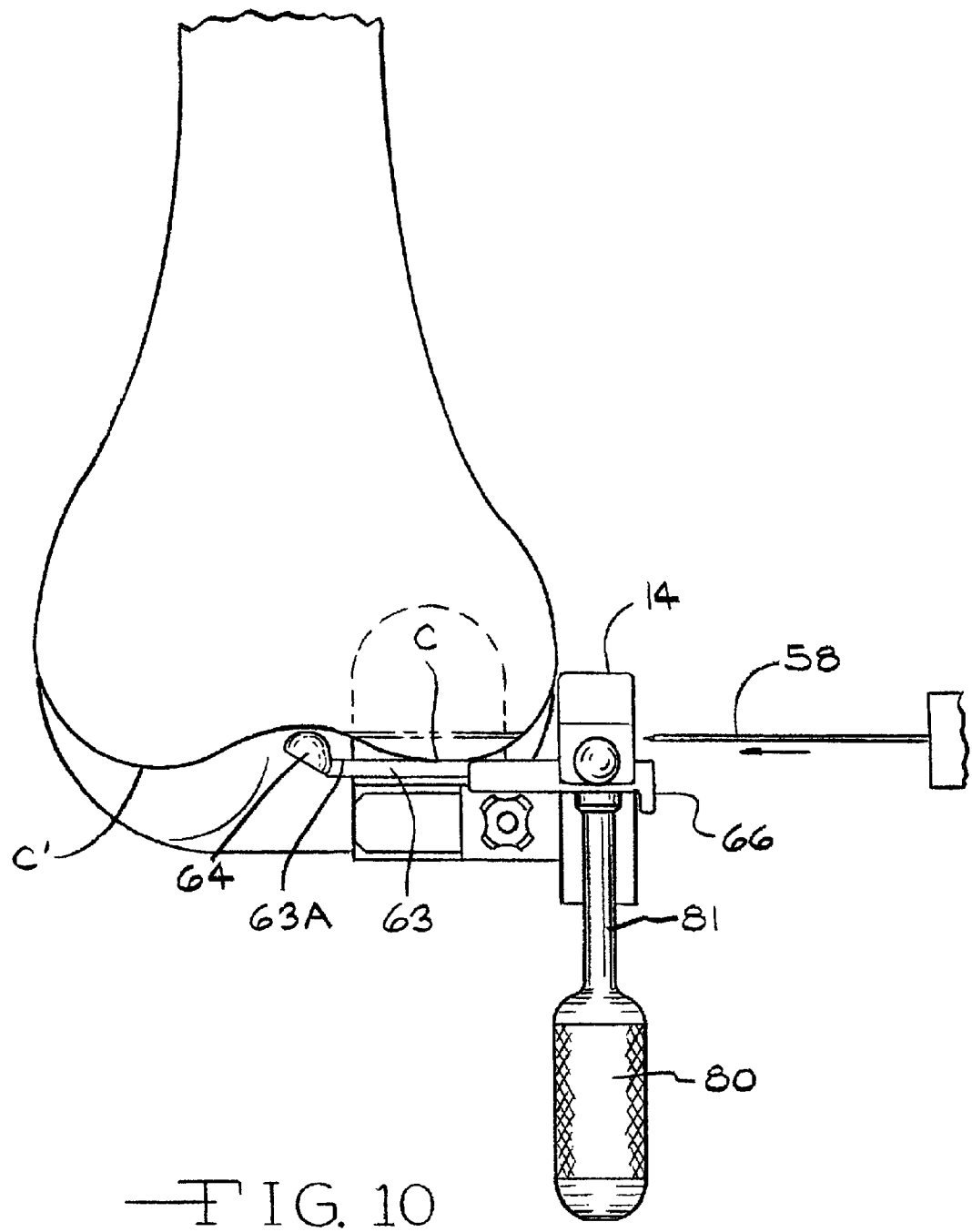
Figures 11, 12:
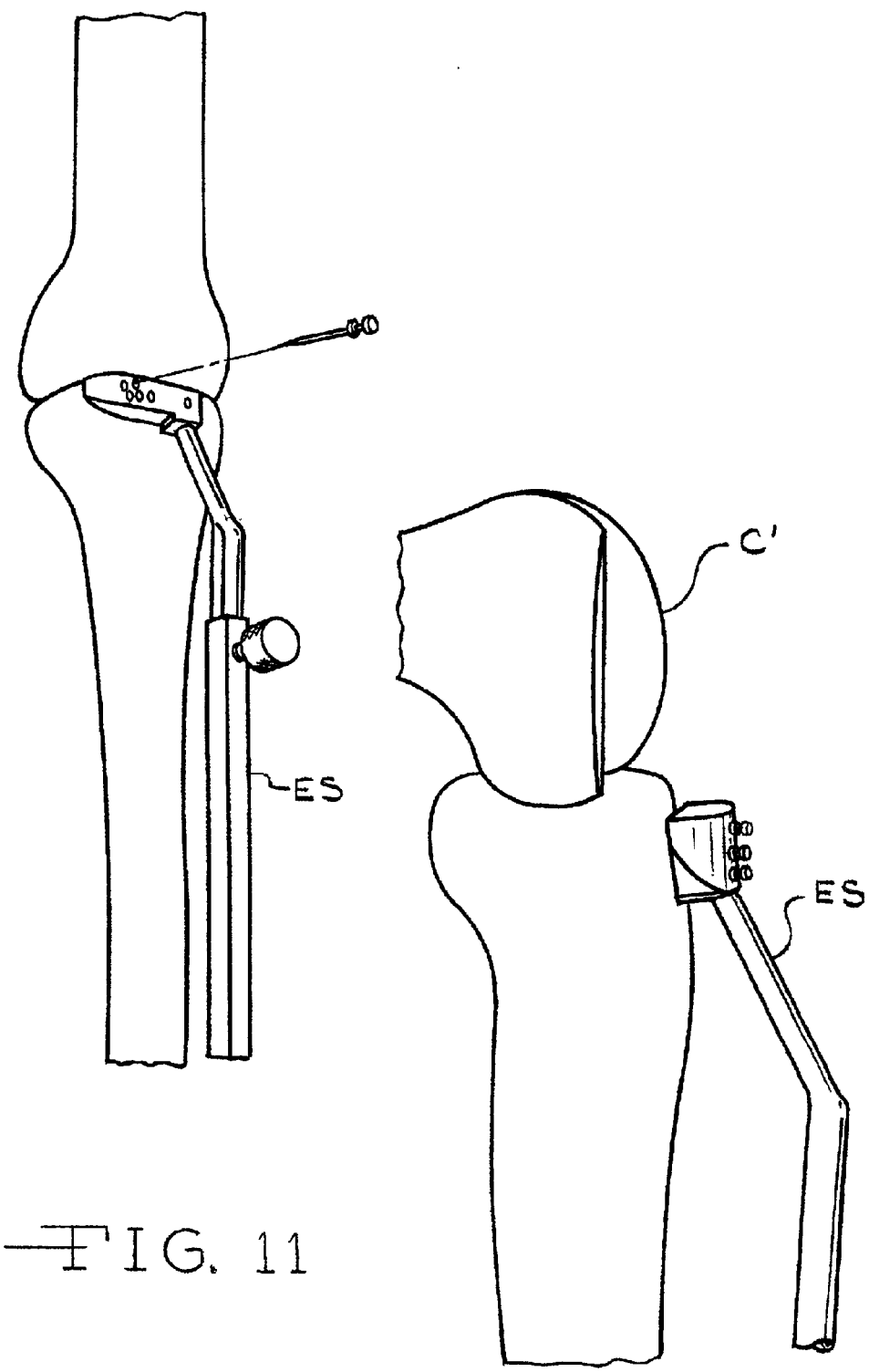

FIGS. 7 and 10 show an arm assembly 60 and the positioning of the surface 63A of the reduced size arm 63 relative to the connector portion 61 for a patient for whom it is desired to remove 6 millimeters from the end of the condyle C. As can be seen from FIGS. 7 and 10 the surface 63A is flush with the surface 61A of the connector portion and is in contact with the distal end of the condyle C. Thus, assuming that the distance from the bottom of the recess 21 to the guide slot 26 is 6 millimeters, a saw 58 would remove 6 millimeters from the distal end of the condyle C when the surface 63A is positioned against such distal end.

Figure 8:
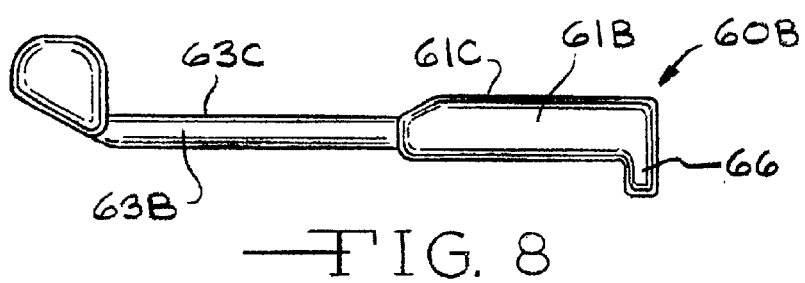
FIG. 8 is a view of an alternate arm for determining a different depth of cut for a condyle.
Figure 5:
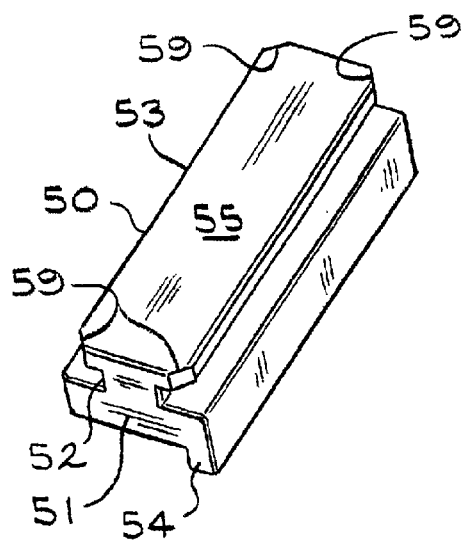
FIGS. 5 and 6 are perspective views from different angles of the base member for attaching the cutting guide assembly to a support member.
Figure 6:
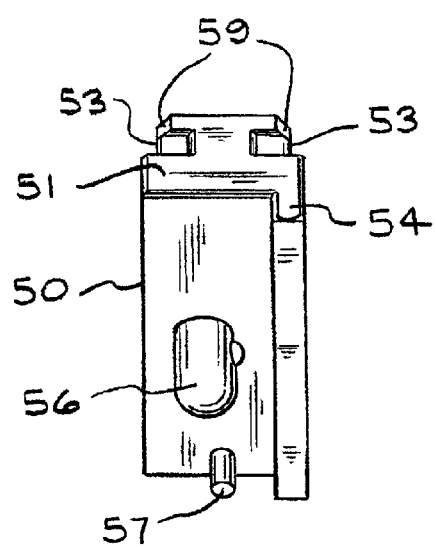

If it is desired to remove an additional thickness of the condyle C, the arm assembly 60 of FIG. 7 could be replaced by the arm assembly 60B of FIG. 8. The arm assembly of FIG. 8 has a reduced size arm 63B with a surface 63C intended to engage the distal end of the condyle which is spaced inwardly from the surface 61C of the connector portion 61B which engages the bottom of the recess 21. Thus, for the arm assembly 60B of FIG. 8, the distance from the surface 63C engaging the distal end of the condyle C to be cut and the plane of the guide slot receiving the saw 58 is 8 millimeters. Other arm assemblies with different dimensions can be utilized to provide innumerable options for the thickness to be removed from a condyle.

The stylus 64 at the end of the reduced size arm 63 extends into the plane of the guide slot 26 and thus serves as a stop preventing movement of the saw 58 beyond that point thereby protecting the opposing condyle C' from unintended cutting.

The stylus 64 also serves an additional function for those patients whose condyle being cut has been excessively worn away. In positioning the saw guide assembly 10, one of the adjustments will be to move the arm assembly 60 laterally relative to the saw guide 14 to position the stylus 64 in alignment with the sulcus of the patient. It is important that the cutting of the condyle C not be of such a depth as to extend into the sulcus. Accordingly, if a patient's condyle which is to be cut has worn to an excessive degree such that desired thickness of condyle, say 6 millimeters, is not available to be cut, the surface 63A will not contact the distal end of such condyle C. Rather, the stylus 64 will contact the sulcus and the cut will be made relative to the position of the stylus 64 against the sulcus rather than relative to the surface 63A relative to the distal end of the condyle.

If it is desired to remove both condyles, the saw guide 14 may be used with an arm assembly which does not have a stylus or other structure extending into the plane of travel of the saw. In that case, the surgeon, after removal of the first condyle can simply continue movement of the saw to cut the second condyle without other movement or relocation of the cutting guide assembly 10.

Referring now to FIGS. 14–18 there is shown a modified cutting guide assembly 110 which is capable of being adjusted both (i) medially/laterally and (ii) proximately/distally. This is in contrast to the previous embodiment which could be adjusted only in the medial/lateral direction. This embodiment includes many features of the embodiment of FIGS. 1–8 which will not be repeated here.

Under the present embodiment, the cutting guide assembly 110 has a cutting guide 114 having a generally similar shape to the cutting guide 14 of the previous embodiment and having a recess 121 similar to the recess 21 of the previous embodiment for receiving the arm assembly 60. It also has a circular hole or recess 128 (see FIG. 17) in the end 117 for receiving the stub 73 of the first support tower 25 and a rectangular hole 132 in the front 116 for receiving the stub of the second support tower 31. A slot 126 for receiving and guiding a saw extends completely through the saw guide 114 from the front 116 to the back.

As in the embodiment of FIGS. 1–8, the arm assembly 60 is slideably adjustable in the recess 121 of the cutting guide and is retained therein by a handle 180, stem 181 and shoulder 182 assembly threadedly engaged to the cutting guide 114. However, in this embodiment, the handle 180 has, adjacent its free end, a short length 188 having a reduced diameter and an enlarged head 189 outwardly therefrom. The short length 188 and enlarged head 189 provide means for readily engaging the handle 180 with a component of a slap hammer.

In order to provide for proximal/distal adjustment, the saw guide 114 includes an integrally formed unitary extension 184 extending outwardly from the recess 121 and the second planar wall section 120 at substantially a right angle to the wall section 120. The extension 184, in cross section, is provided with a pair of inturned flanges 186 spaced from the upper panel 185 of the extension. The inturned flanges 186 are spaced apart from each other and provide a structure for slideably receiving a combination adjustment member 190 shown in detail in FIG. 18. The combination adjustment member 190 is so named because it has means for accommodating both medial/lateral adjustment and proximal/distal adjustment. It is provided with a pair of outwardly extending flanges 191 spaced upwardly from a flat surface 192 to provide grooves in which the inturned flanges 186 of the extension 184 may fit thus permitting the combination adjustment member 190 to be moved relative to the cutting guide 114 to provide adjustment in the proximal/distal direction. An aperture 187 extends through the upper panel 185 and receives a pin which is positioned therein following engagement of the combination adjustment member 190 to the extension 184. The end of the pin is received in a slot 196 of the combination adjustment member 190 and assists in guiding the combination adjustment member as it is moved in a proximal/distal direction in the extension 184.

The second adjustment feature afforded by the combination adjustment member 190 results from its inturned flanges 193 which are spaced apart and spaced from the adjacent undersurface to define a pair of slots 194 having a size to receive the wings 53 of the base member 50. The path of travel defined by the slots 194 is at substantially a right angle to the path of travel of the outwardly extending flanges 191 moving in slots defined by the inturned flanges 186 of the extension 184. The foregoing second adjustment feature provides for adjustment in the medial/lateral direction. A threaded aperture 197 extends through the panel defined by the flat surface 192 and receives a threaded pin/knob assembly 198 for use in retaining the assembly 110 to the base 50.

FIG. 19 is a perspective view of a foot guide generally designated by the numeral 100. For certain types of operations, it is preferable not to rely upon an additional or external support member. Thus, it is possible to utilize the cutting guide assembly of the present invention without relying upon any such external support even though such external support is preferred in most cases. The foot guide 100 is specifically designed to assist in the use of the cutting guide assembly 10 or the modified cutting guide assembly 110 when those instruments are used without such external support. The foot guide 100 is an L-shaped member and includes a slideable engagement portion 111 intended to be positioned in a medial/lateral direction relative to the patient and sized to receive either the plate 15 of the embodiment of FIGS. 1–8 or the combination adjustment member 190 of the embodiment of FIGS. 14–19. The engagement portion 111 has outwardly extending flanges 115 sized to be received in slots 40 of the plate 15 or slots 194 of the combination adjustment member 190.

Extending at a 90° angle to the slideable engagement portion 111 is a toe member 112 extending to a nose 113 which follows an arcuate path from the major portion of the toe. Except for the nose portion 113, the toe member has a thickness in the range of 0.030 to 0.187 inch. The nose portion 113 tapers from that to a thinner thickness at the crest of the nose on the order of 0.020 inch. In use, the toe 112 starting with the arcuate nose portion 113, is positioned under the distal end of the femur adjacent the condyle which is to be cut and is held in place by the wedging action between the distal end of the femur and the proximal end of the tibia. With the foot guide 100 so positioned and the cutting guide assembly 10 or 110 engaged thereto, the surgeon, following medial/lateral adjustment, (and proximal/distal adjustment for the embodiment of FIGS. 14–18) and appropriate alignment of the alignment rods 72 and 77, may proceed with cutting the condyle.

Figure 20:
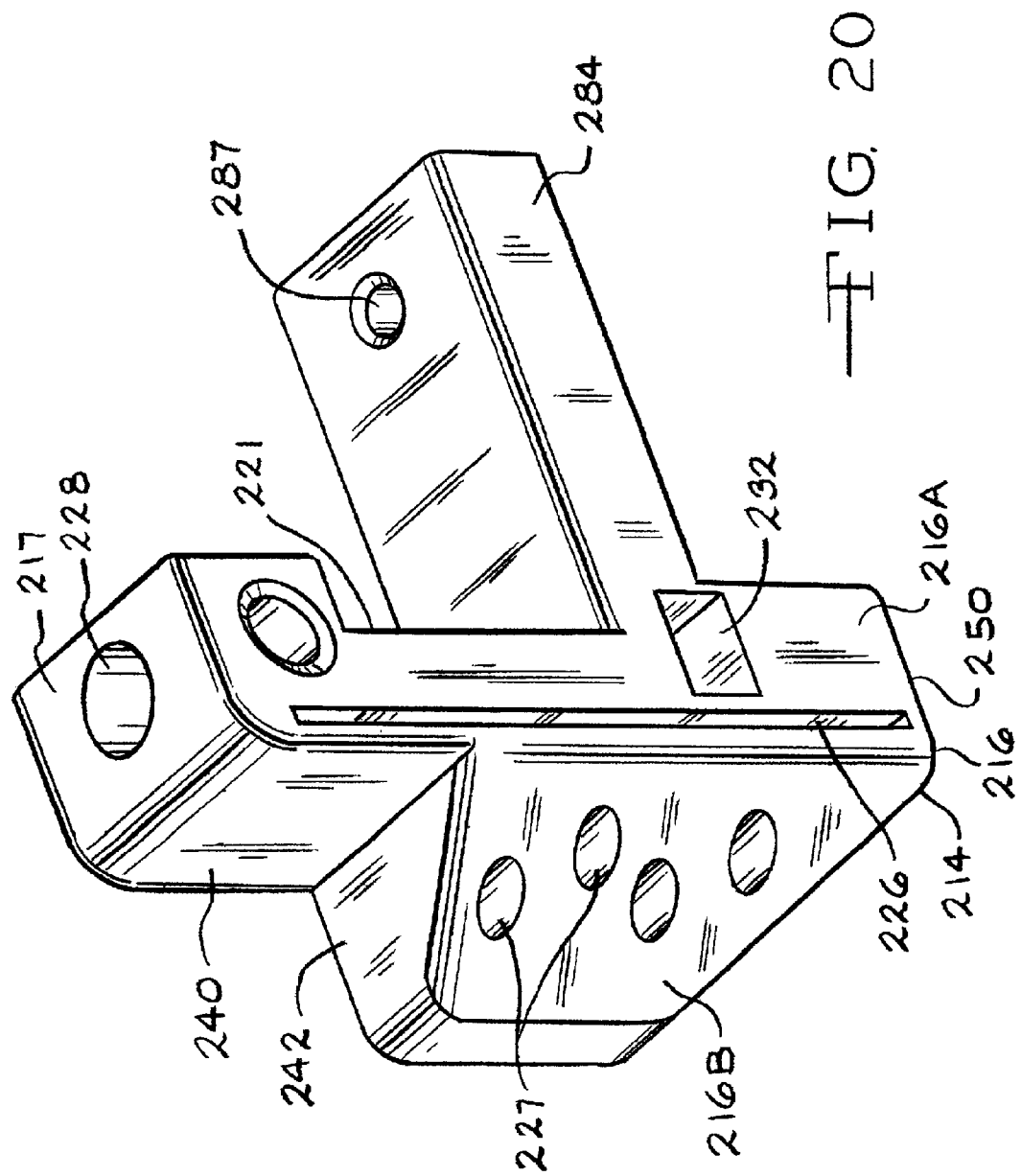
FIG. 20 is a perspective view of yet another modified cutting guide unit.
Figure 21:
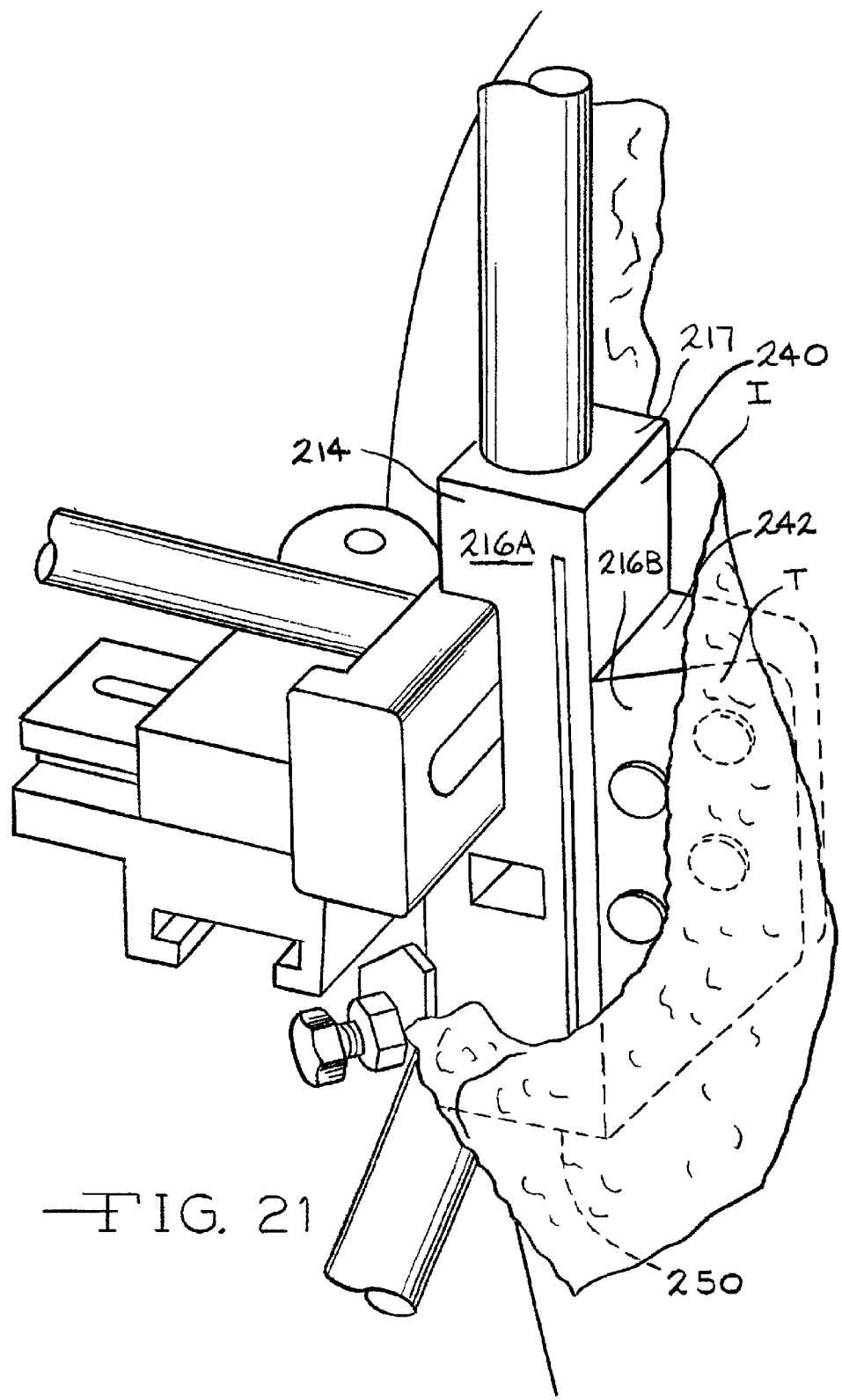
FIG. 21 is a perspective view of a cutting guide assembly with the modified cutting guide unit of FIG. 21 in use during surgery.

Referring to FIGS. 20 and 21, there is provided a modified cutting guide 214 similar to the cutting guide 114 of the embodiment of FIGS. 14–17 in that it is capable of being adjusted both (i) medially/laterally and (ii) proximally/distally. As such, it is provided with a unitary extension 284 integrally formed with the remainder of the cutting guide and extending outwardly from a recess 221 similar to the recess of the previous embodiment for receiving the arm assembly 60. It also has a circular hole or recess 228 in the end 217 for receiving the stub 73 of the first support tower 25. The cutting guide 214 differs from the cutting guide 114 of the embodiment of FIGS. 14–17 in that it has a front 216 which is divided into two sections, namely, a first front section 216A lying on a first plane and a second front section 216B which is disposed at an angle on the order of 45°±20° from the plane of the first front section 216A. The first front section 216A is provided with a rectangular hole 232 for receiving the stub of the second support tower 31. A slot 226 is provided for receiving a saw such as the saw 58 shown in FIG. 10. The slot 226 extends throughout the thickness of the cutting guide 214 from the first front section 216A through the back surface.

A plurality of holes 227 extend through the guide 214 from the second front wall section 216B to the back and are positioned to receive pins with which the surgeon may fasten the cutting guide 214 to the lateral or medial aspect of the knee undergoing the surgical procedure.

The advantage of tapering the second front wall section 216B at an angle on the order of 45°±20° to the first front wall section 216A is that it provides a relief and avoids adverse impingement of soft tissue during the surgical procedure. This may be seen in FIG. 21 which shows the cutting guide 214 in use with the remaining components of an assembly. FIG. 21 shows the cutting guide 214 in the incision I of a patient. The side of the cutting guide 214 opposite the first and second front wall sections 216A and 216B is positioned against the medial or lateral side of the knee undergoing surgery. The incision I results in loose soft tissue T. As a result of the tapering of the second front wall section 216B, the soft tissue T adjacent the incision I in the area of the second front wall section 216B, there is provided a space for the soft tissue T thereby avoiding adverse impingement of such soft tissue T during the surgical procedure.

It will be noted that the portion of the cutting guide 214 containing the second front section 216B does not extend to the end 217 but rather extends only about ⅔ of the distance from the first end 250 to the end 217 having the circular hole or recess 228. There is thus provided a planar or flat land 240 extending from the end 217 toward the opposing end 250 and a wall 242 extending therefrom at substantially right angles. This provides an additional area of relief for the soft tissue.

Many modification will become readily apparent to those skilled in the art. Accordingly, the scope of the present invention should be limited only by the scope of the claims appended hereto.

We claim:

1. A cutting guide assembly for use in performing surgery on the distal end of a condyle of a femur without disrupting the intramedullary canal of said femur comprising
   (i) a guide member having a slot for receiving and guiding a saw along a path defining a first plane, said slot positioned to guide said saw to cut in a medial to lateral direction or lateral to medial direction; and
   (ii) an arm assembly extending from said guide member, said arm assembly including (a) an arm surface engageable with the distal end of a condyle to be cut, said arm surface lying in a second plane spaced from said first plane and (b) a stylus extending into said first plane to limit the extent to which a saw extending through said slot can travel.

2. A cuffing guide assembly according to claim 1 further including an attachment member on said guide member engageable with a supplementary guide attached to a patient's tibia.

3. A cutting guide assembly for use in performing surgery on the distal end of a condyle of a femur comprising
   (i) a guide member having a slot for receiving and guiding a saw along a path defining a first plane; and
   (ii) an arm assembly extending from said guide member, said arm assembly including (a) an arm surface engageable with the distal end of a condyle to be cut, said arm surface lying in a second plane spaced from said first plane and (b) a stylus extending into said first plane to limit the extent to which a saw extending through said slot can travel, wherein said stylus being sized relative to said guide member so as to be aligned with the sulcus between the condyle to be cut and the opposing condyle when said guide member is positioned against the lateral or medial aspect of said femur with said slot facing the lateral or medial aspect of said condyle to be cut.

4. A cutting guide assembly for use in performing surgery on the distal end of a condyle of a femur comprising
   (i) a guide member having a slot for receiving and guiding a saw along a path defining a first plane;
   (ii) an arm assembly extending from said guide member, said arm assembly including (a) an arm surface engageable with the distal end of a condyle to be cut, said arm surface lying in a second plane spaced from said first plane and (b) a stylus extending into said first plane to limit the extent to which a saw extending through said slot can travel; and
   (iii) a first support tower engaged to said guide member;
   (iv) a first alignment rod supported on said first support tower, movement of said first alignment rod to a position generally parallel to the anatomical axis of said femur moving said saw guide assembly to a partially aligned position;
   (v) a second support tower engaged to said guide member; and
   (vi) a second alignment rod supported on said second support tower movement of said second alignment rod to a position generally parallel to said femur in the coronal plane as viewed in flexion extension moving said saw guide assembly to a fully aligned position with said first plane being substantially perpendicular to the mechanical axis of said femur.

5. A cutting guide assembly for use in performing surgery on the distal end of a condyle of a femur comprising
   (i) a guide member having a slot for receiving and guiding a saw along a path defining a first plane; and
   (ii) an arm assembly extending from said guide member said arm assembly including (a) an arm surface engageable with the distal end of a condyle to be cut, said arm surface lying in a second plane spaced from said first plane and (b) a stylus extending into said first plane to limit the extent to which a saw extending through said slot can travel, said arm assembly being moveably mounted relative to said guide member and further including a connector member adjustable to (A) permit movement of said arm assembly relative to said guide member and (B) fixedly secure said arm assembly to said guide member.

6. A cutting guide assembly for use in performing surgery on the distal end of a condyle of a femur comprising
   (i) a guide member having a slot for receiving and guiding a saw along a path defining a first plane; and
   (ii) an arm assembly extending from said guide member said arm assembly including (a) an arm surface engageable with the distal end of a condyle to be cut, said arm surface lying in a second plane spaced from said first plane and (b) a stylus extending into said first plane to limit the extent to which a saw extending through said slot can travel, said arm assembly being mounted for movement relative to said guide member, said movement being lateral or medial to said condyles when said guide member is positioned on the lateral or medial aspect of the patients knee.

7. A cutting guide assembly for use in performing surgery on the distal end of a condyle of a femur comprising
   (i) a guide member having a slot for receiving and guiding a saw along a path defining a first plane;
   (ii) an arm assembly extending from said guide member, said arm assembly including (a) an arm surface engageable with the distal end of a condyle to be cut, said arm surface lying in a second plane spaced from said first plane and (b) a stylus extending into said first plane to limit the extent to which a saw extending through said slot can travel, and
   (iii) an attachment member engageable with a supplementary guide engaged to a patient's tibia or to a patient's distal femur, said attachment member including an adjustment track permitting movement of said guide member relative to said supplementary guide.

8. A cutting assembly according to claim 7 wherein said arm assembly is mounted for movement relative to said guide member, said movement being lateral or medial to said condyles when said guide member is positioned on the lateral or medical aspect of the patient's knee.

9. A cutting assembly according to claim 7 wherein said supplementary guide is a foot guide having a toe engageable with said distal femur.

10. A cutting assembly according to claim 9 wherein said foot guide includes a track engageable with said cutting guide assembly, said track permitting movement of said cutting guide assembly laterally or medially of said femur when said toe is engaged to said distal femur.

11. A cutting guide assembly for use in knee surgery for cutting one or both condyles at the distal end of a femur having an anatomical axis and a mechanical axis comprising
   (A) a guide having a first side with a face engageable with the medial or lateral aspect of a knee, said guide including an elongated slot for receiving a saw, said elongated slot extending through said guide from said first side to an Opposing second side, a saw extending through said slot positioned to cut medially to laterally or laterally to medially along a cutting path when said face is so engaged,
   (B) a first alignment support engaged to said guide;
   (C) a second alignment support engaged to said guide;
   (D) a first alignment rod engaged to said first alignment support; and
   (E) a second alignment rod engaged to said second alignment support,
   the positioning of
   (a) said first alignment rod to a position substantially parallel to the anatomical axis of said femur; and
   (b) said second alignment rod to a position substantially parallel to said femur as viewed in flexion extension,
   aligning said guide to a position such that a saw extending through said slot will be substantially perpendicular to the mechanical axis of said femur.

12. A cutting guide assembly for use in knee surgery for cutting one or both condyles at the distal end of a femur having an anatomical axis and a mechanical axis comprising
   (A) a guide having a first side with a face engageable with the medial or lateral aspect of a knee, said guide including an elongated slot for receiving a saw, said elongated slot extending through said guide from said first side to an opposing second side, a saw extending through said slot positioned to cut medially to laterally or laterally to medially along a cutting path when said face is so engaged,
   (B) a first alignment support engaged to said guide;
   (C) a second alignment support engaged to said guide;
   (D) a first alignment rod engaged to said first alignment support;
   (E) a second alignment rod engaged to said second alignment support; and
   (F) an arm assembly extending from said guide, said arm assembly including a surface spaced from and substantially parallel to said cutting path.

13. A cutting guide assembly according to claim 12 wherein said arm assembly includes a stylus extending into said cutting path.

14. A cutting guide assembly according to claim 12 wherein said arm assembly is adjustably movable on said guide.

15. A cutting guide assembly for use in knee surgery for cutting one or both condyles at the distal end of a femur having an anatomical axis and a mechanical axis comprising
   (A) a guide having a first side with a face engageable with the medial or lateral aspect of a knee, said guide including an elongated slot for receiving a saw, said elongated slot extending through said guide from said first side to an opposing second side, a saw extending through said slot positioned to cut medially to laterally or laterally to medially along a cutting path when said face is so engaged,
   (B) a first alignment support engaged to said guide;
   (C) a second alignment support engaged to said guide;
   (D) a first alignment rod engaged to said first alignment support; and
   (E) a second alignment rod engaged to said second alignment support,
   characterized in that said first alignment support is removably supported on said guide and cooperates therewith to define a fixed angle between said cutting path and said first alignment rod.

16. A cutting guide assembly for use in knee surgery for cutting one or both condyles at the distal end of a femur having an anatomical axis and a mechanical axis comprising
   (A) a guide having a first side with a face engageable with the medial or lateral aspect of a knee, said guide including an elongated slot for receiving a saw, said elongated slot extending through said guide from said first side to an opposing second side, a saw extending through said slot positioned to cut medially to laterally or laterally to medially along a cutting path when said face is so engaged,
   (B) a first alignment support engaged to said guide;
   (C) a second alignment support engaged to said guide;

(D) a first alignment rod engaged to said first alignment support; and (E) a second alignment rod engaged to said second alignment support, characterized in that said first alignment support includes (a) an aperture in said cutting guide, said aperture including a flat surface; and (b) a support tower having an end stub sized to be received in said aperture, said end stub having a flat surface engageable with said aperture flat surface, said support tower having a hole for receiving said first alignment rod, said hole lying on an axis disposed at an angle relative to a plane defined by said stub flat surface.

17. A guide assembly according to claim 16 wherein said angle is in the range of 1° to 10°.

18. A cutting guide assembly for use in knee surgery for cutting one or both condyles at the distal end of a femur having an anatomical axis and a mechanical axis comprising (A) a guide having a first side with a face engageable with the medial or lateral aspect of a knee, said guide including an elongated slot for receiving a saw, said elongated slot extending through said guide from said first side to an opposing second side, a saw extending through said slot positioned to cut medially to laterally or laterally to medially along a cutting path when said face is so engaged, (B) a first alignment support engaged to said guide;

(C) a second alignment support engaged to said guide;

(D) a first alignment rod engaged to said first alignment support; and (E) a second alignment rod engaged to said second alignment support, (F) a base member adjustably secured to said cutting guide, said base member including an adjuster permitting movement of said base member relative to said cutting guide medially to laterally or laterally to medially;

(G) an external support adapted to be attached to the tibia adjacent said femur; and (H) a protuberance on said base member engageable with said external support.

19. A cutting guide assembly for use in knee surgery for cutting one or both condyles at the distal end of a femur having an anatomical axis and a mechanical axis comprising (A) a guide having a first side with a face engageable with the medial or lateral aspect of a knee, said guide including an elongated slot for receiving a saw, said elongated slot extending through said guide from said first side to an opposing second side, a saw extending through said slot positioned to cut medially to laterally or laterally to medially along a cutting path when said face is so engaged, (B) a first alignment support engaged to said guide;

(C) a second alignment support engaged to said guide;

(D) a first alignment rod engaged to said first alignment support; and (E) a second alignment rod engaged to said second alignment support, (F) a foot guide having a first portion positioned to engage the distal end of said femur or said condyle and a second portion engageable with said cutting guide, said cutting guide movably adjustable on said foot guide medially to laterally or laterally to medially.

20. A cutting guide assembly for use in knee surgery for cutting one or both condyles at the distal end of a femur having an anatomical axis and a mechanical axis comprising (A) a guide having a first side with a face engageable with the medial or lateral aspect of a knee, said guide including an elongated slot for receiving a saw, said elongated slot extending through said guide from said first side to an opposing second side, a saw extending through said slot positioned to cut medially to laterally or laterally to medially along a cutting path when said face is so engaged, (B) a first alignment support engaged to said guide;

(C) a second alignment support engaged to said guide;

(D) a first alignment rod engaged to said first alignment support;

(E) a second alignment rod engaged to said second alignment support;

(F) an extension on said guide disposed at substantially a right angle relative to said culling path; and, (G) a combination adjustment member engageable with said extension for effecting adjustment in the proximal/distal direction and engageable with an external support member disposed in a fixed position relative to said femur distal end for effecting adjustment in the medial/lateral direction.

21. A cutting guide assembly in accordance with claim 20 wherein said combination adjustment member includes a first track slideably engaged to said extension and a second track disposed at substantially a right angle to said first track, said second track being slideably engaged to said external support member.

22. A culling guide assembly in accordance with claim 21 wherein said external support member is a foot guide, said foot guide having a first portion positioned to engage the distal end of said femur or said condyle and a second portion engageable with said combination adjustment member second track.

23. A cutting guide assembly for use in knee surgery for cutting one or both condyles at the distal end of a femur having an anatomical axis and a mechanical axis comprising (A) a guide having a first side with a face engageable with the medial or lateral aspect of a knee, said guide including an elongated slot for receiving a saw, said elongated slot extending through said guide from said first side to an opposing second side, a saw extending through said slot positioned to cut medially to laterally or laterally to medially along a cutting path when said face is so engaged, (B) a first alignment support engaged to said guide;

(C) a second alignment support engaged to said guide;

(D) a first alignment rod engaged to said first alignment support; and (E) a second alignment rod engaged to said second alignment support, characterized in that said guide second side includes a first segment substantially parallel to said first side and a second segment tapering away from said first segment and toward said first side.

24. A cuffing guide assembly in accordance with claim 23 wherein said first segment defines a first plane and said second segment defines a second plane disposed at an angle of 45° plus or minus 20° to said first plane and said slot passes through said first segment.

25. A cutting guide assembly for use in knee surgery for cutting one or both condyles at the distal end of a femur having an anatomical axis and a mechanical axis comprising (a) a guide having a first side with a face engageable with the medial or lateral aspect of a knee, said guide including an elongated slot for receiving a saw, said elongated slot extending through said guide from said first side to an opposing second side, a saw extending through said slot being positioned to cut medially to laterally or laterally to medially along a cutting path when said face is so engaged, (b) a first alignment support engaged to said guide;

(c) a second alignment support engaged to said guide;

(d) a connector for adjustably securing said guide to an external support member disposed in a fixed position relative to said femur distal end, said connector permitting movement of said guide relative to said external support member medially to laterally or laterally to medially;

(e) a first alignment rod engaged to said first alignment support; and (f) a second alignment rod engaged to said second alignment support.

26. A cutting guide assembly in accordance with claim 25 wherein said connector includes a base member having a pair of tracks slideably engageable to said external support member.

27. A cutting guide assembly in accordance with claim 25 wherein said guide includes an extension disposed in a proximal/distal direction when said slot is positioned to cut medially to laterally or laterally to medially and said connector includes a combination adjustment member having a first track slideably engaged to said extension and a second track disposed at substantially a right angle to said first track, said second track being slideably engaged to said external support member.

28. A method of performing surgery on one or both condyles of a knee having first and second condyles at the distal end of a femur comprising the steps of (a) providing a cutting guide having a slot for receiving a saw blade, said blade when extending through said slot defining a first plane, first and second guide posts on said cutting guide, said first and second guide posts having means for receiving first and second guide rods, respectively, and an arm assembly having a surface lying on a second plane parallel to and spaced from said first plane;

(b) positioning said cutting guide such that said slot is facing said first condyle from the lateral or medial aspect;

(c) supporting said cutting guide externally of said femur;

(d) moving said cutting guide to align said first guide rod to a position parallel to the anatomical axis of said femur and said second guide rod to a position parallel to said femur as viewed in flexion extension; and (e) moving said blade through said slot to cut the distal end from said first condyle in a medial to lateral direction or lateral to medial direction.

29. The method of claim 28 further including the step of positioning said arm assembly surface against the distal end of said first condyle prior to cutting said first condyle distal end.

30. The method of claim 28 wherein said arm assembly includes a distal end disposed away from said second plane and extending into said first plane and further including the step of positioning said arm assembly distal end between said first condyle and said second condyle.

31. The method of claim 28 further including the steps of (i) determining the angle between the mechanical axis and anatomical axis of said femur, (ii) engaging to said cuffing guide a first guide post having engagement means for receiving said first guide rod, said engagement means providing angular orientation to said cutting guide based upon said angle such that said first plane will be substantially perpendicular to said mechanical axis when said first guide rod is parallel to said anatomical axis.

32. The method of claim 28 further including the steps of providing an external support on the tibia adjacent said femur and further including the step of engaging said cutting guide to said external support.

33. The method of claim 32 further including the step of moving said cuffing guide laterally or medially following the steps of engaging said cuffing guide to said external support.

34. The method of claim 33 further including the step of moving said cutting guide along a line generally parallel to said anatomical axis.

35. The method of claim 28 further including the steps of (i) providing a foot member having a first portion engageable with said cutting guide and a second portion extending therefrom and (ii) engaging said first portion to said cutting guide and said second portion to the distal end of said femur or one of said condyles.

36. The method of claim 28 further including the step of continuing movement of said blade along the plane of the path traversed by said blade in step (e) to cut the distal end of said second condyle.

37. A method for performing knee surgery at the distal end of a femur having a first condyle and a second condyle spaced therefrom comprising the steps of (a) providing a cutting guide having a slot for receiving and guiding a cutting instrument, said cutting instrument, when extending therethrough, following a path defining a first plane;

(b) positioning said cutting guide in a position with said slot facing the distal end of said first condyle from the medial or lateral aspect;

(c) supporting said cutting guide in said position externally of said femur; and (d) cutting said first condyle distal end by moving said cutting instrument in a medial to lateral direction or in a lateral to medial direction.

38. The method of claim 37 further including the step of moving of said cutting instrument through said slot following step (d) to cut said second condyle.

39. The method according to claim 37 further including the step of blocking said first plane in the space between said first condyle and second condyle.

40. The method according to claim 37 wherein said cutting guide has an entrance side and an exit side and a blocking element extending into said first plane on said exit side and spaced from said exit side and further including the step of positioning said blocking element in the space between said first and second condyles.

41. The method according to claim 37 wherein said cutting guide includes a first support for a first guide rod and a second support for a second guide rod and further including the steps of aligning said first guide rod parallel to the anatomical axis of said femur and said second guide rod parallel to said femur when viewed in flexion extension.

42. The method according to claim 37 wherein said cutting guide includes first engagement means for receiving a first support for a first guide rod and second engagement means for receiving a second support for a second guide rod, said first support cooperating with said first engagement means to compensate for the angular difference between the anatomical axis and mechanical axis of said femur and further including the steps of aligning said first guide rod parallel to said anatomical axis and said second guide rod parallel to said femur when viewed in flexion extension.

43. The method according to claim 42 wherein there is provided a plurality of first supports for said first guide rods, each of said plurality, when cooperating with said first engagement means, compensating for one of a plurality of said angular differences and further including the steps of ascertaining said angular difference and engaging to said cutting guide the one of said plurality of first supports which most closely corresponds to said angular difference.

44. The method according to claim 37 further including the step of engaging said cutting guide to an external support engaged to a tibia adjacent said femur.

45. The method according to claim 37 further including the steps of providing a support member engageable with the distal end of said femur and further including the steps of engaging said support member to said distal end or one of said condyles and of engaging said cutting guide to said support member.

* * * * *

UNITED STATES PATENT AND TRADEMARK OFFICE
CERTIFICATE OF CORRECTION

PATENT NO. : 6,770,077 B2
DATED : August 3, 2004
INVENTOR(S) : Van Zile et al.

Page 1 of 1

It is certified that error appears in the above-identified patent and that said Letters Patent is hereby corrected as shown below:

Column 10,
Line 5, please delete "cuffing" and insert -- cutting --;
Line 48, after "tower" please insert -- , --;
Line 58, after "member" please insert -- , --;

Column 11,
Line 7, after "member" please insert -- , --;
Line 17, please delete "patients" and insert -- patient's --;
Line 54, please delete "Opposing" and insert -- opposing --;

Column 14,
Line 32, please delete "culling" and insert -- cutting --;
Line 60, please delete "cuffing" and insert -- cutting --.

Signed and Sealed this

Twelfth Day of April, 2005

JON W. DUDAS
*Director of the United States Patent and Trademark Office*